(12) United States Patent
Keller et al.

(10) Patent No.: US 7,820,444 B2
(45) Date of Patent: Oct. 26, 2010

(54) METHOD FOR SAMPLE IDENTIFICATION IN A MAMMAL AS WELL AS A KIT FOR PERFORMING THIS METHOD

(76) Inventors: Ruprecht Keller, Geisbergstrasse 90, 50939 Koln (DE); Gisela Gauchel, Husenbergweg 42, 53332 Bornheim (DE)

(*) Notice: Subject to any disclaimer, the term of this patent is extended or adjusted under 35 U.S.C. 154(b) by 1125 days.

(21) Appl. No.: 10/471,815

(22) PCT Filed: Mar. 14, 2002

(86) PCT No.: PCT/EP02/02868

§ 371 (c)(1), (2), (4) Date: Dec. 2, 2003

(87) PCT Pub. No.: WO02/075307

PCT Pub. Date: Sep. 26, 2002

(65) Prior Publication Data

US 2004/0166532 A1    Aug. 26, 2004

(30) Foreign Application Priority Data

Mar. 15, 2001 (DE) .................................. 101 12 470

(51) Int. Cl.
- *G01N 31/00* (2006.01)
- *G01N 33/00* (2006.01)
- *G01N 33/53* (2006.01)
- *G01N 33/566* (2006.01)
- *C12Q 1/00* (2006.01)
- *C12Q 1/06* (2006.01)

(52) U.S. Cl. .................. 436/15; 424/9.1; 424/9.411; 424/10.1; 424/156; 424/178.1; 424/184.1; 424/278.1; 424/439; 435/4; 435/7.1; 435/7.95; 435/39; 436/8; 436/13; 436/501

(58) Field of Classification Search ............ 422/70; 424/124; 435/287.1; 436/8, 13, 14, 15, 74, 436/161, 174

See application file for complete search history.

(56) References Cited

U.S. PATENT DOCUMENTS 4,017,616 A * 4/1977 Gomez et al.

(Continued)

FOREIGN PATENT DOCUMENTS

GB    2 271 848 A    4/1994

(Continued)

OTHER PUBLICATIONS

Bjarnason et al. 1994. Scand. J. gastroenterol. vol. 29: 630-639.*

(Continued)

*Primary Examiner*—Mark Navarro
*Assistant Examiner*—JaNa Hines
(74) *Attorney, Agent, or Firm*—Foley & Lardner LLP

(57) ABSTRACT

Method as well a kit for the performance of the method for the investigation of biological samples from a mammal for at least one component, wherein the method includes the following steps: (a) Administering at least one marker substance to a mammal; (b) Waiting for a length of time which is sufficient for the at least one marker substance to reach the location of sample removal; (c) Removing a biological sample from the mammal; (d) Investigating the biological sample for the presence and/or amount of at least one marker substance or a derivative thereof; and, if the at least one marker substance or the derivative thereof is detectable in the biological sample; (e) Investigating the biological sample for an analyte.

28 Claims, 3 Drawing Sheets

Marker A

U.S. PATENT DOCUMENTS

| | | |
|---|---|---|
| 4,953,562 A | 9/1990 | Rosen et al. |
| 5,024,231 A | 6/1991 | Feldschuh et al. |
| 5,039,616 A | 8/1991 | Copelan |
| 5,093,265 A | 3/1992 | Portman et al. |
| 5,179,027 A | 1/1993 | Fisher |
| 5,531,682 A | 7/1996 | Mazer et al. |

FOREIGN PATENT DOCUMENTS

| | | | |
|---|---|---|---|
| GB | 2 320 960 A | | 7/1998 |
| JP | 2000-28614 | | 1/2000 |
| WO | WO 98/12557 | * | 3/1998 |
| WO | WO 98/14275 | | 4/1998 |
| WO | WO 98/18003 | | 4/1998 |
| WO | WO 99/36775 | | 7/1999 |
| WO | WO 99/56789 | | 11/1999 |
| WO | WO 00/74781 A1 | | 12/2000 |

OTHER PUBLICATIONS

Donovan et al. 1990. Pharm. Res. vol. 7(9):863-868.*
He et al. 1998. J. of Phar. Sci. vol. 87(5): 626-633.*
Miki et al. 1996. Clin. Chem. vol. 42(1): 71-75.*
Philipsen et al, 1988. Eur. J. of Clin. Investigations. vol. 18: 139-145.*
Ukabam et al. 1984. Digestive Diseases and sciences. vol. 29(9): 809-816.*
Philipsen et al. 1988. Eur. J. of Clin. Investigations. vol. 18: 139-145.*
Philipsen et al. 1988. Eur. J. of Clin. Investigations. vol. 18: 139-145.*

* cited by examiner

Marker A

Marker B

Marker C

METHOD FOR SAMPLE IDENTIFICATION IN A MAMMAL AS WELL AS A KIT FOR PERFORMING THIS METHOD

The present invention relates to a method by which a sample which was taken from an excretion, a body fluid of a mammal or as a tissue sample, can be identified with relation to the origin of the sample and, in this way, can be unequivocally assigned to the donor of the sample, whereby the sample can be investigated for an analyte. Additionally, the object of the invention is a kit for performing this method.

Diagnostic methods, methods for monitoring the course of a therapeutic measure, prophylactic routine investigations as well as forensic medical investigations on man normally include the analytical investigation of samples in the laboratory, such as for example blood or serum samples which were taken from the subject, as well as the investigation of excretions of the subject, such as for example urine. In view of the multitude of existing medical diagnosis and therapy methods for animals, a very wide variety of analytical methods with animal samples is today every bit as much common practice as well. Especially the problems having arisen in connection with intensive livestock farming, such as BSE sicknesses due to the feeding of animal meal or the admixing of illegal food additives in the form of hormones and/or antibiotic preparations into the mast of livestock necessitate an extension of regular control investigations in animal herds in agriculture.

In this context there is no question that any analytical investigation of a sample is only then meaningful if the results obtained in the investigation can also be unequivocally assigned to the respective donor of the sample in order to then initiate the correct response in evaluating the experimental results.

New analysis and test methods are continuously being developed as part of scientific-technical progress. Advances in molecular biology for example allow the implementation of a series of detection methods based on DNA analysis, by which certain sicknesses in man or in animals can be diagnosed.

Many newer analysis and detection methods also find application in forensic medicine or, due to constantly more challenging tasks of the latter, owe their development to it, for example specific testing methods for the detection of doping substances in athletes or for the detection of drugs in vehicle drivers.

Due to the multitude of analysis methods implemented as well as their complexity, high standards are expected of the technical equipment as well as of the personnel in the laboratories who perform these investigations. Normally many samples have to be investigated simultaneously with modern analysis apparatus so that the problem of a mix-up of samples unavoidably arises, thereby leading to an incorrect assignment of the investigation results with respect to the sample donor. This problem is not new and is even exacerbated especially by the rapid development of new analysis methods and the associated growing need for their use.

Since the consequences of a mix-up or an exchange of the samples to be analyzed are different but normally undesirable, there already exist a whole series of suggestions as to how to solve this problem.

These attempts at solutions relate mainly to an improved organization of the workflow in an investigative laboratory, where the following of certain rules of behavior is intended to minimize the danger of sample mix-up. However, since many protocol steps in these analysis methods are carried out by laboratory personnel themselves, mix-ups attributable to human error cannot be completely ruled out.

Knowing this, computer-controlled monitoring of the respective protocol steps to be performed with the sample is widely used, for example by labeling the sample vessels with a computer-readable code so that the respective sample can be tracked during the entire investigation process, beginning with entry of the sample and including the processing and storage of the experimental results. This computer-monitored and computer-controlled sample analysis therefore allows a large number of parallel determinations of different samples without a significant danger of mix-ups.

It is however clear to one of ordinary skill in the art that even the cleverest system of monitoring the samples to be investigated in a laboratory and of assigning the test results to these samples and, with this assignment, to the sample donors, cannot completely exclude a mix-up or an exchange of the samples, since only an inadequate marking of the samples or of the test results thereof can take place.

The described problem of a mix-up or an exchange of samples is especially heightened in fields of application in which the test results can be used as incriminating evidence against the sample donor or, in the case of a sample originating from a livestock animal, against the owner of the animal. In these cases there exists a special interest of the subject or of the owner to tamper with the test samples in order to avoid the generation of incriminating evidence.

However, it is especially in these cases that an unequivocal assignment of the test results to the sample donor are especially important, since certain legal regulations can often only be enforced in this way.

The attempts at solutions which, in view of this problem, already exist in the prior art for preventing tampering with the sample relate exclusively to the monitoring of sample removal. For example it is common practice that the submission of urine from subjects taking part in methadone therapy is supervised.

However, even the most clever monitoring and supervision of subjects during the submission of the urine sample will not completely prevent an exchange of the samples. In Germany 20,000 of the 120,000-140,000 drug addicts are already treated with methadone. A major increase in this number is to be expected in the future. Since methadone patients often take other narcotics as well as barbiturates and tranquilizers, a control of the substances taken by the patients is therapeutically necessary.

According to the guidelines for the implementation of methadone therapy, the urine must be checked at least once a week or, under certain circumstances, even more frequently. Normally, submission of the urine sample under observation is not possible in normal doctors' offices since commonly only a small restroom is present and normally male medical personnel are not at adequate disposal to accompany the male methadone patients. The construction of restrooms suitable for sample submission under observation requires a high financial outlay. Just the costs for such investment in the health office of Duesseldorf came to 50 TDM.

Due to the commonly observed tampering of submitted urine samples, work is increasingly being done on analysis methods for detection of drugs in saliva discharge. Even if, in contrast to using blood, plasma or urine as test samples, a saliva sample can be obtained without a damaging intrusion or without intruding upon the subject's privacy, the danger of a negligent mix-up of or an intentional tampering with the samples still cannot be prevented.

The goal of the present invention is therefore to ensure an unequivocal assignment of the samples to the donor and, in this way, to overcome the problems or disadvantages common to the prior art.

According to the invention this goal is met by providing a method for the investigation of biological samples from a mammal for at least one component, wherein the method includes the following steps:
(a) Administering at least one marker substance to a mammal;
(b) Waiting for a length of time which is sufficient for the at least one marker substance to reach the location of sample removal;
(c) Removing a biological sample from the mammal;
(d) Investigating the biological sample for the presence and/or amount of at least one marker substance or a derivative thereof; and, if the at least one marker substance or the derivative thereof is detectable in the biological sample;
(e) Investigating the biological sample for an analyte.

Figure 1:
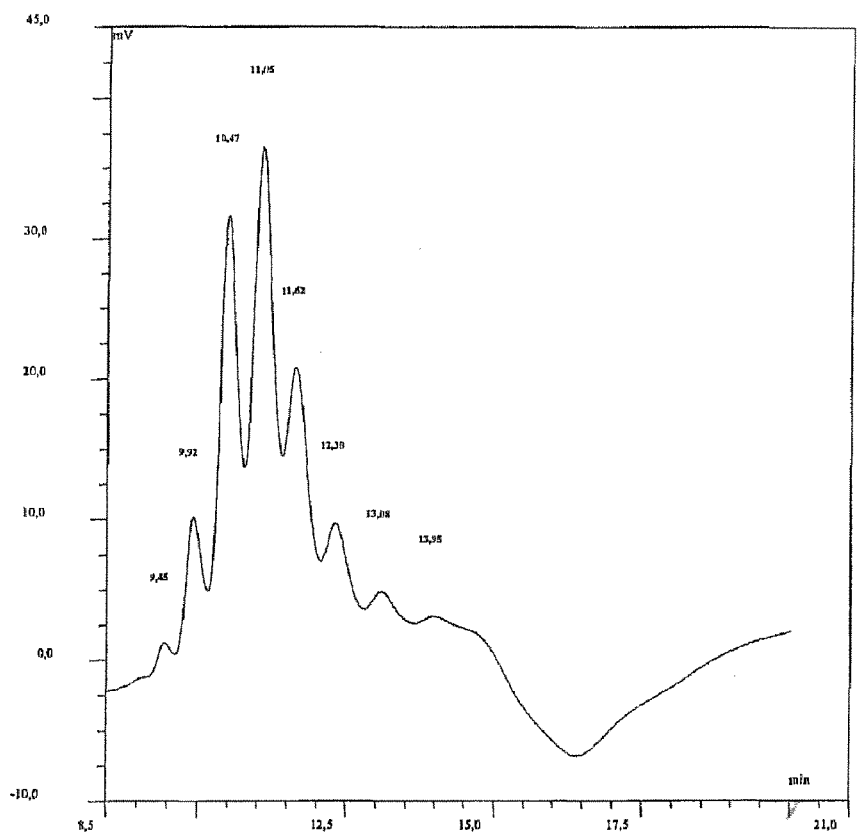
FIG. 1 shows the results of a chromatographic elution pattern of "Marker A" (PEG 400) of a urine sample as described in Example 2. The results show that Marker A can be used as a marker substance for identification of a urine sample from a specified donor.

The idea of the present invention was therefore to find a possibility with which the sample to be investigated can be marked while preventing this marker from being removed from the sample by methods accessible to a layperson. The method is therefore suitable for example for monitoring methadone therapy as well as for doping checks. Advantageous marking substances are in general characterized by a series of specific characteristics. These marker substances exert no pharmacological side effects on the organism of the mammal at the concentrations which are necessary for detection of these marker substances in the blood, in the urine or other body fluids or in body excretions according to the invention.

A derivative which is specifically formed from the at least one marker substance can also just as well be used in place of the latter. By "derivatives" are to be understood all subsequent products which arise as a result of a chemical transformation in the organism of the subject or in the removed sample, wherein however all subsequent products are excluded which are not exclusively attributable to the transformation of a specific marker in the subject organism or in the removed sample.

It is advantageous if the marker substances are soluble in a liquid, that the normal taste of the liquid such as for example juice is not changed by the addition or that, following dissolving in water, no unpleasant taste of the resulting solution is caused by the marker substances and, therefore, the subject can willingly drink the liquid containing the markers.

Advantageous marker substances are characterized in that they are absorbed quickly through the intestinal mucous membranes and are excreted from the subject in the urine. It is further advantageous if these marker substances in urine samples can be detected in as simple a manner as possible by detection methods already established in chemical investigation laboratories such as for example common methods of clinical analytical chemistry. According to the invention, it is preferable to use marker substances which are not metabolized following uptake by the subject.

Preferred marker substances are sugars or sugar derivatives such as for example arabinose, erythrulose, myo-inositol, cis-inositol, mannitol, sorbose, rhamnose, sorbitol, xylose and xylulose, which are soluble in water and which can be easily detected by enzymatic tests.

It is also advantageous to use isoprenoids, lipids, saccharides, polyols, polyethylene glycols, derivatives or mixtures of these substances as the marker substance.

Especially preferred is the use of the method according to the invention in the investigation of urine samples. For this, the marker substance or a combination of multiple marker substances is dissolved in a liquid, and the liquid is orally administered in that the subject drinks the liquid approximately 30 to 60 minutes before the urine submission. Polyethylene glycols or mixtures thereof are most preferably used as marker substances for the investigation of urine samples.

It is especially preferable to administer multiple marker substances simultaneously, wherein it is possible by the combination of marker substances to develop a certain numerical code belonging to a respective sample. In order to increase the safety against tampering, it is preferred to administer a combination of at least 2, especially preferred of at least 3, very especially preferred of 5 marker substances simultaneously.

Using a total of n marker substances, there exist $2^n-1$ different combinations in a dual numeric system. Tampering with the samples by the subject is therefore impossible since the subject would have to know the chemical nature of the marker substances, the numerical code for his urine sample and the sequence of marker substances according to which the code is constructed.

The administration of the marker substance can be accomplished in different ways. By "administration" is to be understood the introduction of one or a multitude of marker substances into the organism of the sample donor. According to the invention, the marker substance or the multitude of marker substances can be administered to the sample donor preferably parenterally or orally. It is especially preferred that the marker substance or the multitude of marker substances be taken up via the digestive tract and that, during uptake, no metabolization of the marker substances takes places.

Depending on the type of the at least one marker substance administered and the type of the sample to be removed, it is necessary prior to the removal of the sample to be investigated to wait a certain "sufficient length of time" before sample removal. This length of time represents the time which the at least one marker substance requires to reach the location of sample removal. In the case of sample removal from a component existing separately from the sample donor, such as for example sample removal from a body excretion, the time is to be understood as being that time which is required until the at least one marker substance is present in the separable component and this component is separated from the sample donor. The amount of time one must wait can be empirically determined, wherein however in most cases the corresponding values or methods for their determination are known in the prior art (van Rossum, J. M.: Kinetics of Drug Action. Handbuch der experimentellen Pharmakologie, Vol. 47. Springer, Berlin 1977; Forth, W.: Allgemeine und spezielle Pharmakologie und Toxikologie. Bibliographisches Institut & F. A. Brockhaus, Mannheim 1988).

Sample removal occurs in different ways depending on the type of sample to be investigated. In the case of the analysis of body excretions, part of the sample is taken up into a sample vessel and, after this time, is ready for further investigation. In the investigation of human urine or stool samples, the samples can usually be furnished by the subjects themselves in that the subject is simply given a sample vessel. For the removal of samples from body fluids or from tissue samples, a direct operation on the subject is normally necessary. Here, obtention of blood from the subject can be accomplished using a suction pipette following pricking or cutting of the skin with a disposable lancet or—in larger quantities—using an injection syringe or blood collection tube (German: Venule) after puncture of the vein. For the investigation of liquor, the latter is obtained by lumbar, suboccipital or ventricle puncture.

By "biological sample" is meant the components of a mammal designated for the analytical investigation. Relevant here are body excretions, body fluids or tissue samples. The components making up the sample can include components of a mammalian organism which still exist in the mammal at the time of sample removal as well as previous components of the mammal.

By "body excretions" or "excretion" are to be understood urine, stool, secretions from salivary, milk, tear and sweat glands.

By "body fluid" are to be understood extracellular liquids of a mammalian organism like blood, serum and liquor.

By "mammal" are to be understood in addition to animals of this category man as well.

Preferably, the samples removed from or excreted by a mammal are body excretions, body fluids or tissue samples.

By "tissue sample" is to be understood an organization of identically differentiated cells obtained by a direct operation into the living mammalian organism, as well as these cells' intercellular substance. Hair samples and samples of sloughed-off parts of skin are also to be understood as falling within the meaning of this term.

Depending on the type of the sample and the at least one marker substance to be detected, the respective sample has to be prepared prior to the analysis method. The preparation steps can include centrifugation for the separation of solid, non-solubilized materials in a liquid sample such as for example urine, solubilization or suspension of solid samples such as for example stool, concentration by ion-exchange chromatography using Centricons, by precipitation with suitable reagents such as ammonium sulfate, adjustment of the pH value required for the analysis method, homogenization of the sample such as by ultrasonication or by using vibration cell mills in order to, for example, be able to investigate components from originally intact tissues, separation of materials used in lysing the sample such as for example detergents and other preparation steps known to one of ordinary skill in the art.

A number of enzymatic, immunological, mass-spectroscopic and electrophoretic detection methods as well as combinations of these methods are available for the determination of the presence or absence of at least one marker substance in a sample. Preferably, detection is accomplished by a coupled Gas Chromatography/Mass Spectrometry (GC/MS) or High Performance Liquid Chromatography/Mass Spectrometry (HPLC/MS) method or by High Performance Liquid Chromatography (HPLC) or Gas Chromatography (GC). These methods allow the very time-efficient investigation of, in particular, liquid samples or of samples which, due to their preparation were transferred into a liquid. At the same time, these detection methods allow a high degree of automatization so that a multitude of samples can be analyzed in a short time and, in as far the chromatograms and, as the case may be, mass spectroscopic fractionation patterns of reference substances already exist in the computer evaluation unit, the actual detection of the at least one marker substance is also greatly simplified.

If it is determined as a result of the evaluation of the analysis method applied that the originally administered at least one marker substance is present in the investigated sample, then this allows the unequivocal assignment of this sample to the subject. If this requirement is fulfilled, i.e. that the sample originates from the subject being investigated, the actual investigation of this sample or, alternatively, of a second sample for an analyte takes place.

By "analyte" is to be understood at least one chemical substance, wherein the knowledge as to the presence or, as the case may be, also of its concentration in the sample, allows a conclusion as to a past, expected or present condition of the sample donor. As an example, a conclusion as to an incorrectly functioning—because incomplete—resorption of glucose from the urine by the kidney tubules (glucosuria) in a subject is made possible on the basis of knowledge of the concentration of an analyte such as for example the glucose concentration in the urine of a urine sample, which was normally enzymatically determined by means of glucose oxidase (GOD) or hexokinase. Analytes can further be intoxicants, medicines, metabolites of the previously named substances, the detection of which in the sample yields information as to the behavior or a treatment of the subject.

In addition to the use of the method according to the invention in human medicine, there also exist a multitude of further applications in the veterinary medical field and in agriculture. The method can advantageously be used in the monitoring of adherence to regulations for the use of feed additives in agricultural livestock mast farming.

If for example samples obtained from mast pigs are to be investigated for the presence of growth hormones or antibiotics or their metabolites, the use of the method according to the invention can avoid the problem of a tampering with the samples to be investigated by the owner of the herd of mast pigs.

Here, especially those marker substances are advantageous which remain in the animal over a long length of time—in the ideal case over the entire duration of masting—yet which are still continuously present in a detectable amount, for example in a body excretion. For this reason, those marker substances are advantageous which can be administered to the animal as a time-release agent, by virtue of which for example a time-delayed yet continuous resorption through the intestinal mucous membranes takes place and therefore the at least one marker substance is detectable over a longer length of time, for example in a body excretion like animal feces. Especially suitable samples are samples with which both the investigation for the at least one marker substance as well as the detection or the concentration determination of at least one analyte takes place.

Another object of the present invention is a kit for performing the described method for sample identification in a mammal, wherein the kit according to the invention includes a marker substance in a container such as a tablet vessel as well as, as the case may be, means for administering the at least one marker substance to the mammal.

It is especially advantageous if this kit also contains at least one reference substance for the detection of the marker substance or the multitude of marker substances.

A kit according to the invention preferably contains, for the oral administration of the marker substances, these marker substances in the form of individual water-soluble effervescent tablets. Alternatively, these effervescent tablets can also already contain the marker substances as mixtures of multiple marker substances. The respective substance code can then be taken from the label of the tablet vessel.

The kit can comprise effervescent tablets with varying concentrations of marker substances corresponding to the circle of people to whom the marker is to be administered, so that these marker substances can be applied for example to children as well as adults without reaching a concentration of marker substances in the subject at which pharmacological side effects can arise.

It is especially advantageous if the tablet vessels contained in the kit are provided with a computer-readable code. Kits intended for the marking of urine samples of methadone patients preferably contain tablets, capsules, or similar application forms in which both the amount of methadone to be administered as well as the mixture of marker substances are available together.

Further advantageous embodiments of the kit according to the invention include multiple reference substances by means of which the marker substances can be easily identified in the chromatographic analysis of the sample, such as for example in the investigation of the urine sample.

In, for example, the investigation of the urine sample of a patient treated with methadone, an ampoule tube can also be present in the kit according to the invention, which ampoule tube contains a mixture of marker substances solubilized in a suitable carrier means according to the chosen chromatographic method, wherein this mixture corresponds exactly to the mixture present in the corresponding methadone tablets.

By a subsequent run on the same GC column, it can be determined very quickly and with certainty due to the chromatography peaks of the marker substances in a GC analysis whether the investigated urine sample originates from the patient being treated with methadone.

EXAMPLE 1

For the further exemplary explanation of the method according to the invention, an embodiment for performing the marking of a sample to be investigated is provided below.

The embodiment relates to the marking of a urine sample to be investigated and its subsequent investigation. The subject receives 100-300 ml of liquid to drink, in which 1 g polyethylene glycol 600 is solubilized as a marker substance. Fruit juices, water, and other liquids palatable to humans can be used as liquids to drink.

In place of polyethylene glycol 600, monodisperse fractions or mixtures of monodisperse fractions can also be used. Here, the laboratory establishes a substance code. Such a code is given in the following as five monodisperse polyethylene glycol fractions. Here, "0" stands for not present and "1" stands for present.

| Substances Code | Substances | | | | |
|---|---|---|---|---|---|
| | A | B | C | D | E |
| 1 | 0 | 0 | 0 | 1 | 1 |
| 2 | 0 | 0 | 1 | 0 | 1 |
| 3 | 0 | 0 | 1 | 1 | 0 |
| 4 | 0 | 0 | 1 | 1 | 1 |
| 5 | 0 | 1 | 0 | 0 | 1 |
| 6 | 0 | 1 | 0 | 1 | 0 |
| 7 | 0 | 1 | 0 | 1 | 1 |
| 8 | 0 | 1 | 1 | 0 | 0 |

-continued

| Substances Code | Substances | | | | |
|---|---|---|---|---|---|
| | A | B | C | D | E |
| 9 | 0 | 1 | 1 | 0 | 1 |
| 10 | 0 | 1 | 1 | 1 | 0 |
| 11 | 1 | 0 | 0 | 0 | 1 |
| 12 | 1 | 0 | 0 | 1 | 0 |
| 13 | 1 | 0 | 0 | 1 | 1 |
| 14 | 1 | 0 | 1 | 0 | 0 |
| 15 | 1 | 0 | 1 | 0 | 1 |
| 16 | 1 | 0 | 1 | 1 | 0 |
| 17 | 1 | 1 | 0 | 0 | 0 |
| 18 | 1 | 1 | 0 | 0 | 1 |
| 19 | 1 | 1 | 0 | 1 | 0 |
| 20 | 1 | 1 | 1 | 0 | 0 |

The substances A, B, C, D and E correspond to polyethylene glycol fractions with molecular weights:

| A | 530 |
|---|---|
| B | 574 |
| C | 618 |
| D | 662 |
| E | 706 |

After ingestion the subject was requested to wait at least 30 minutes and at the most 4 hours before urinating. The subject was allowed to consume further liquids or solid food during this waiting phase. The subject did not have to be supervised during the waiting time. The submission of urine by the subject took place without supervision.

The sample vessel was identified with a barcode label coding a job number also contained on the computer-readable accompanying tag. On the accompanying tag were noted the name of the subject, the desired investigation as well as the combination of marker substances or the substance code. The sender is saved by the job number in the master data of the lab computer. The samples were transported to the laboratory with the accompanying tag. The accompanying tag was entered into the computer with a card reader. The job was recorded in this way. Here, the substance combination or the substance code was also entered into the computer.

For the analysis for polyethylene glycol, the urine was centrifuged, 100 µl of the supernatant was given on Nucleosil C 100-(C18), 3 µm (4.6×125 mm) at a flow rate of 0.5 ml/min (methanol/water 5/95) and was investigated for polyethylene glycol by detection with an Refractive Index (RI) detector. The chromatography peaks were identified as polyethylene glycols by the retention times based on the reference chromatographies.

In this way, each investigated urine sample could be unequivocally assigned to the respective subject via the substance code of the different polyethylene glycol fractions used. The subject was subsequently investigated for the analyte, i.e. an intoxicant to be detected like heroin or its derivatives.

Sugars for marking body fluids can be used in the same manner as described for polyethylene glycol fractions. These are determined from urine or other body fluids via enzymatic detection reactions. The analytical detection methods required for this are known in the prior art (Methods of Enzymic Analysis, ed. Bergmeyer, H. U. VCH Verlagsgesellschaft mbH, Weinheim 1986).

EXAMPLE 2

For pre-analytical patient preparation, patients of drug ambulances were given 1 ml of polyethylene glycol 400 ("Marker A"), 600 ("Marker B") or a mixture of 400 and 600 ("Marker C") in 100 ml fruit juice. Patients were supervised while drinking and asked to wait for at least 30 min prior to urine delivery. After that time patients were allowed to urinate without supervision. The urine tube was then labeled and directly transported to the site of analysis.

Before analysis, the sample were prepared as follows: 10 ml urine was centrifuged at 10500×g for 10 min.

Figure 2:
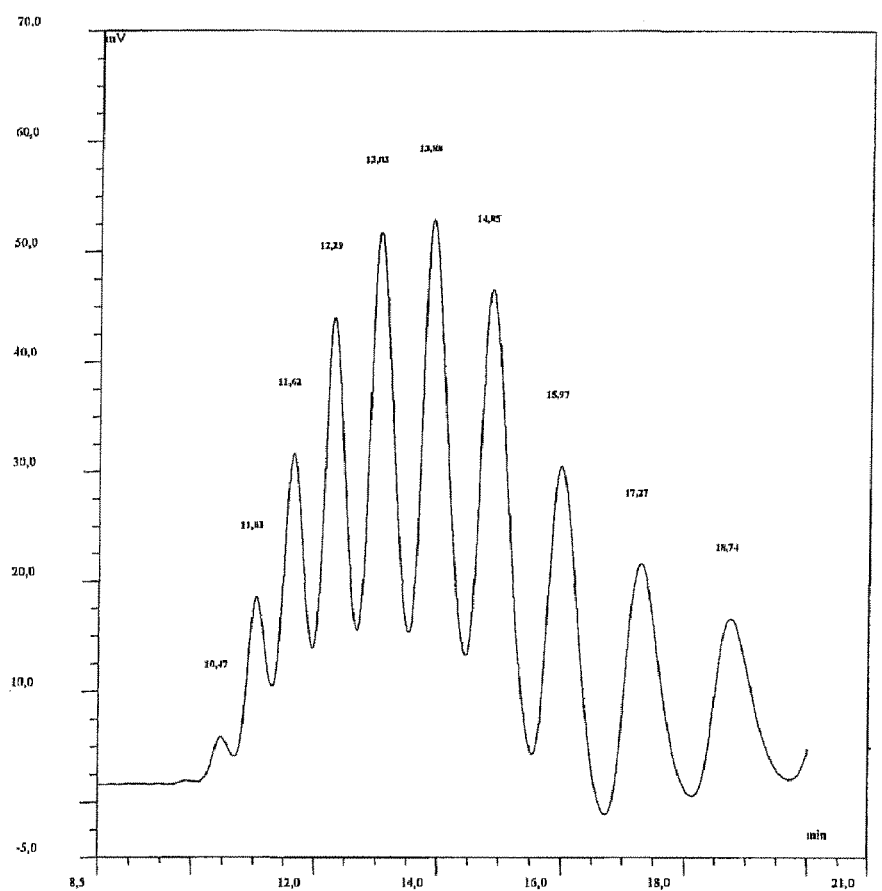
FIG. 2 shows the results of a chromatographic elution pattern of "Marker B" (PEG 600) of a urine sample as described in Example 2. The results show that Marker B can be used as a marker substance for identification of a urine sample from a specified donor.
Figure 3:
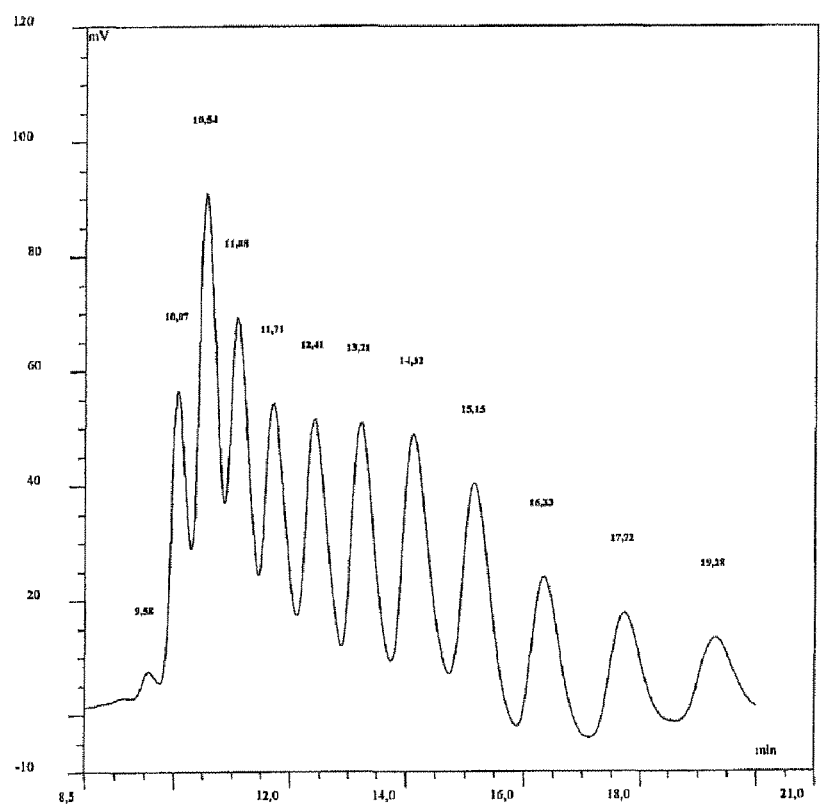
FIG. 3 shows the results of a chromatographic elution pattern of "Marker C" (mixture of PEG 400 and PEG 600) of a urine sample as described in Example 2. The results show that PEG 400 and 600 can be used in combination as marker substances for identification of a urine sample from a specified donor.

For polyethylene glycol analysis, the chromatograph was operated isocratically at ambient temperatures in the column-switching mode. Because RI detection limits to isocratic mobile phases, eluent of cleanup and analytical pump were identical, consisting of 44% methanol and 56% water. 100 µl supernatant of the centrifuged urine were injected automatically onto a (60×4.6 mm) precolumn filled with Nucleosil 100 C18, 5 µm. With the eluent delivered by the clean-up pump at a flow of 0.4 ml/min and a pressure of 36 bar, matrix impurities were discharged to the waste, while the polyethylene glycol (PEG) fractions were retarded on the stationary phase. After 120 sec the precolumn was switched by the six-port valve to the eluent stream of the analytical pump, and the analytes were backflushed for separation with a flow rate of 0.5 ml/min and a pressure of 96 bar onto the analytical column, Nucleosil 100 C8 5 µm. Analysis time took 18 min. Phenomenological characterization of the urinary chromatographic elution pattern was achieved by RI-detection, set at 40° C. According to the observed pattern, markers were then diagnosed as "Marker A", "Marker B" or "Marker C" as shown in the attached FIGS. 1-3.

The following materials and equipments have been used in this example: Polyethylene glycol, PH Eur quality, of the average molecular weight 400 or 600 from Merck, Darmstadt, Germany; HPLC-grade methanol and acetonitrile from Baker; water deionized and purified by Millipore systems Elix3 and MilliQ Gradient A10, Inertsil C8-3 5 µm, (250× 4.6), and Nucleosil 100 C18 5 µm (50×4.6 mm) HPLC columns from Schambeck SFD GmbH, Bad Honnef, Germany. HPLC-Equipment: sample injector S 5200 fitted with a 100 µl injection loop, precolumn clean-up pump S 2100, degaser integrated, six-port motor switching valve ProLAB, column oven SFD 125-600, refraction index detector of deflection type, inline filter element PAT™, for PEEK 3 µm inline filters was obtained from Schambeck SFD GmbH, Bad Honnef, Germany. Analytical pump M480, degassing module degasys DG1310 and data acquisition system Chromeleon 6.11 under Windows NT 4.0 were purchased from Gynkotec.

The invention claimed is:

1. A method for identifying a urine sample as coming from an individual, comprising:
   (a) orally administering two or more polyethylene glycols of different molecular weights to the individual;
   (b) waiting for a length of time sufficient for the polyethylene glycols to be present in the urine of the individual and then collecting a urine sample from the individual;
   (c) investigating the urine sample for the presence of the administered polyethylene glycols to identify the urine sample as coming from the individual; and,
   (d) performing an assay on the urine sample that directly measures the presence or amount of an analyte.

2. The method of claim 1 wherein two polyethylene glycols of different molecular weights are administered.

3. The method of claim 1 wherein three polyethylene glycols of different molecular weights are administered.

4. The method of claim 1 wherein four polyethylene glycols of different molecular weights are administered.

5. The method of claim 1 wherein said length of time is at least 30 minutes and no more than four hours.

6. The method of claim 1 wherein said polyethylene glycols of different molecular weights are detected by means of gas chromatography (GC), gas chromatography/mass spectrometry (GC/MS), high performance liquid chromatography (HPLC) or high performance liquid chromatography/mass spectrometry (HPLC/MS).

7. The method of claim 1 wherein said individual is an athlete.

8. The method of claim 1 wherein said individual is a drug addict.

9. The method of claim 1 wherein said analyte is a drug.

10. The method of claim 1 wherein said analyte is an intoxicant.

11. The method of claim 1 wherein said analyte is a doping substance.

12. The method of claim 10 wherein said intoxicant is heroin.

13. The method of claim 10 wherein said intoxicant is methadone.

14. A method for the investigation of identifying a urine sample as coming from an individual who is a drug addict or athlete, comprising:
   (a) orally administering two or more polyethylene glycols of different molecular weights to the individual;
   (b) waiting for a length of time sufficient for the polyethylene glycols to be present in the urine of the individual and then collecting a urine sample from the individual;
   (c) investigating the urine sample for the presence of the administered polyethylene glycols to identify the urine sample as coming from the individual; and
   (d) performing an assay on the urine sample that directly measures the presence or amount of an analyte selected from the group consisting of a drug, intoxicant and doping substance.

15. The method of claim 14 wherein two polyethylene glycols of different molecular weights are administered.

16. The method of claim 14 wherein three polyethylene glycols of different molecular weights are administered.

17. The method of claim 14 wherein four polyethylene glycols of different molecular weights are administered.

18. The method of claim 14 wherein said individual is addicted to heroin.

19. The method of claim 14 wherein said individual is a methadone user.

20. The method of claim 14 wherein said length of time is at least 30 minutes and no more than four hours.

21. The method of claim 14 wherein said polyethylene glycols of different molecular weights are detected by means of gas chromatography (GC), gas chromatography/mass spectrometry (GC/MS), high performance liquid chromatography (HPLC) or high performance liquid chromatography/mass spectrometry (HPLC/MS).

22. The method of claim 14 wherein said analyte is a drug.

23. The method of claim 14 wherein said analyte is an intoxicant.

24. The method of claim 14 wherein said analyte is a doping substance.

25. The method of claim 23 wherein said intoxicant is heroin.

26. The method of claim 23 wherein said intoxicant is methadone.

27. A method for the investigation of identifying a urine sample as coming from an individual, comprising:
(a) orally administering two or more polyethylene glycols of different molecular weights to the individual;
(b) waiting at least 30 minutes and no more than four hours after administering to collect a urine sample from the individual;
(c) investigating the urine sample for the presence of the administered polyethylene glycols to identify the urine sample as coming from the individual; and
(d) performing an assay on the urine sample that directly measures the presence or amount of an analyte.

28. The method of claim 27 wherein said analyte is selected from the group consisting of a drug, intoxicant and doping substance.

* * * * *